(12) United States Patent
Ayinde et al.

(10) Patent No.: US 12,731,365 B1
(45) Date of Patent: Sep. 8, 2026

(54) AUTOMATICALLY REPORTING ON AN ANATOMICAL STRUCTURE VISUALIZED IN AN ULTRASOUND IMAGE THAT IS SELECTED BY A USER

(71) Applicant: EchoNous, Inc., Redmond, WA (US)

(72) Inventors: Babajide Ayinde, Redmond, WA (US); Matthew Cook, Redmond, WA (US)

(73) Assignee: Echonous, Inc., Redmond, WA (US)

( * ) Notice: Subject to any disclaimer, the term of this patent is extended or adjusted under 35 U.S.C. 154(b) by 0 days.

(21) Appl. No.: 19/179,748

(22) Filed: Apr. 15, 2025

(51) Int. Cl.
*G06V 10/25* (2022.01)
*A61B 8/00* (2006.01)
*A61B 8/08* (2006.01)
*G06V 10/26* (2022.01)
*G06V 10/82* (2022.01)

(52) U.S. Cl.
CPC ............ *G06V 10/25* (2022.01); *A61B 8/0883* (2013.01); *A61B 8/463* (2013.01); *A61B 8/469* (2013.01); *G06V 10/26* (2022.01); *G06V 10/82* (2022.01); *G06V 2201/031* (2022.01)

(58) Field of Classification Search
CPC . A61B 8/00; A61B 8/08; G06V 10/25; G06V 10/82; G06V 10/26
See application file for complete search history.

(56) References Cited

PUBLICATIONS

Kirillov et al., "Segment Anything," 2023 IEEE/CVF International Conference on Computer Vision (ICCV), Paris, France, Oct. 1-6, 2023, pp. 3992-4003. (12 pages).

Ravi et al., "SAM 2: Segment Anything in Images and Videos," arXiv: 2408.00714v2 [cs.CV] Oct. 28, 2024. (42 pages).

Mazurowski et al., "Segment Anything Model for Medical Image Analysis: an Experimental Study," arXiv:2304.10517v3 [cs.CV] May 17, 2023. (21 pages).

Redmon et al., "YOLOv3: An Incremental Improvement," arXiv:1804.02767v1 [cs.CV] Apr. 8, 2018. (6 pages).

Carion et al., "End-to-End Object Detection with Transformers," arXiv:2005.12872v3 [cs.CV] May 28, 2020. (26 pages).

Wang et al., "RepViT: Revisiting Mobile CNN From ViT Perspective," arXiv:2307.09283v8 [cs.CV] Mar. 14, 2024. (12 pages).

Wu et al., "TinyViT: Fast Pretraining Distillation for Small Vision Transformers," arXiv: 2207.10666v1 [cs.CV] Jul. 21, 2022. (21 pages).

Mehta et al., "MobileViT: Light-Weight, General-Purpose, and Mobile-Friendly Vision Transformer," arXiv:2110.02178v2 [cs.CV] Mar. 4, 2022. (26 pages).

Howard et al., "MobileNets: Efficient Convolutional Neural Networks for Mobile Vision Applications," arXiv:1704.04861v1 [cs.CV] Apr. 17, 2017. (9 pages).

Howard et al., "Searching for MobileNetV3," arXiv:1905.02244v5 [cs.CV] Nov. 20, 2019. (11 pages).

*Primary Examiner* — Michael T Rozanski
(74) *Attorney, Agent, or Firm* — Seed Intellectual Property Law Group LLP

(57) ABSTRACT

A facility for presenting automatically generated information about an ultrasound image is described. The facility causes the ultrasound image to be displayed in a display region. Simultaneous to the display of the ultrasound image, the facility causes the following to be displayed in the display region: (1) quantitative data automatically determined for an anatomical feature of interest selected based on user input provided in connection with the display of the ultrasound image, and (2) qualitative data automatically determined for the anatomical feature of interest.

20 Claims, 9 Drawing Sheets

AUTOMATICALLY REPORTING ON AN ANATOMICAL STRUCTURE VISUALIZED IN AN ULTRASOUND IMAGE THAT IS SELECTED BY A USER

BACKGROUND

Ultrasound imaging is a useful medical imaging modality. For example, internal structures of a patient's body may be imaged before, during or after a therapeutic intervention. Also, qualitative and quantitative observations in an ultrasound image can be a basis for diagnosis. For example, ventricular volume determined via ultrasound is a basis for diagnosing, for example, ventricular systolic dysfunction and diastolic heart failure.

A healthcare professional typically holds a portable ultrasound probe, sometimes called a "transducer," in proximity to the patient and moves the transducer as appropriate to visualize one or more target structures in a region of interest in the patient. A transducer may be placed on the surface of the body or, in some procedures, a transducer is inserted inside the patient's body. The healthcare professional coordinates the movement of the transducer to obtain a desired presentation on a screen, such as a two-dimensional cross-section of a three-dimensional volume.

Particular views of an organ or other tissue or body feature (such as fluids, bones, joints or the like) can be clinically significant. Such views may be prescribed by clinical standards as views that should be captured by the ultrasound operator, depending on the target organ, diagnostic purpose or the like.

It is typical for highly-skilled professionals to manually interpret the contents of an ultrasound image captured from a subject to draw conclusions relevant to the health of the patient.

DETAILED DESCRIPTION

Figure 1:
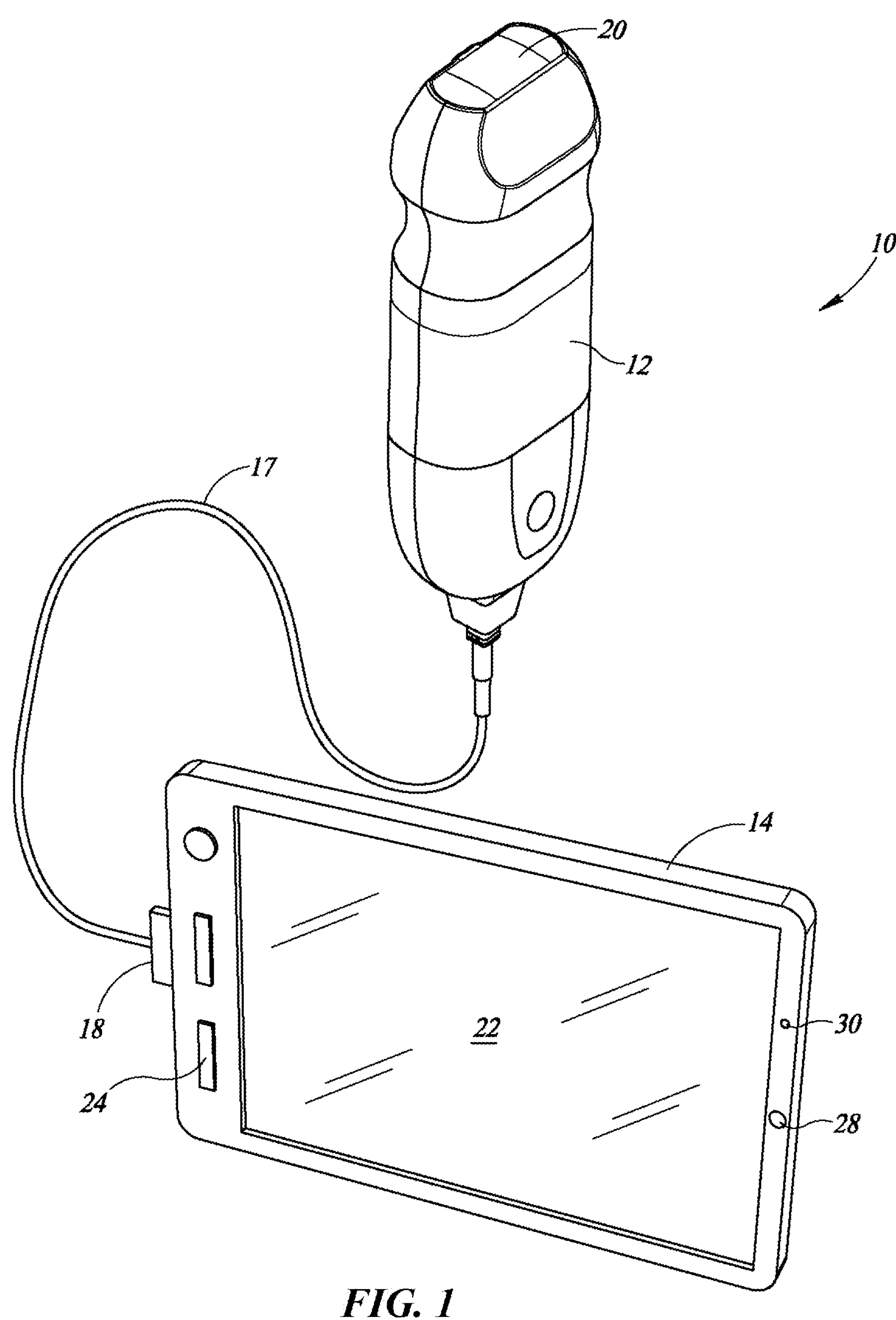
FIG. 1 is a schematic illustration of a physiological sensing device 10, in accordance with one or more embodiments of the present disclosure.

The inventors have recognized that conventional manual approaches to interpreting ultrasound images depend on the availability of a person with significant education and experience at the time the interpretation is needed; requires spending that highly-qualified time on the task; takes a fair amount of time to complete once begun; and can have variable levels of accuracy depending on the person performing it.

In response, the inventors have conceived and reduced to practice a software and/or hardware facility for automatically reporting on an anatomical structure visualized in an ultrasound image that is selected by a user ("the facility").

In some embodiments, the facility captures and displays an ultrasound image of a patient. The facility receives user input selecting an anatomical structure visualized by the image, such as the left ventricle ("LV") of the patient's heart, such as by touching inside the anatomical structure, "scribbling" over at least part of its area; drawing a box, oval, or other shape around it; panning or zooming the image to show it in the center of the image; speaking its name, etc.

In some embodiments, the facility uses the user input as a basis for establishing a bounding box around the selected anatomical structure—i.e., a rectangle containing the anatomical structure, ideally being one of the smallest rectangles containing it. In some embodiments, the facility applies a "bound anything" machine learning model ("BAM") to the image and input as a basis for predicting the bounding box.

In some embodiments, the facility applies a "view and structure" machine learning model ("VASM") to the image and bounding box to predict the structure contained by the bounding box and the view represented by the image.

In some embodiments, the facility applies a "segment anything" machine learning model ("SAM") to the image and bounding box, and in some cases the structure identity and/or view, to predict a segmentation mask for the structure—i.e., the set of pixels of the image that correspond to the structure. The set of pixels specified by the segmentation mask is generally contiguous. In some embodiments, the facility augments the display of the ultrasound image based on the segmentation mask, such as by superimposing the mask's border over the image.

In some embodiments, the facility applies one or more quantitative attribute derivation techniques to the image, segmentation mask, and view and structure to produce one or more quantitative attributes for the structure in the image. For example, for the left ventricle structure, in some embodiments the facility determines some or all of end-diastolic volume (EDV), end-systolic volume (ESV), ejection fraction (EF), wall thickness, strain measurements, and wall motion abnormalities.

In some embodiments, the facility applies one or more qualitative attribute determination tools to the image and data produced about it by the facility to derive one or more qualitative attributes from the image in the structure, such as a disease or pathology classification, sometimes including confidence score and/or explanation. In some embodiments, at least some of the qualitative attribute classification tools are classifying machine learning models, such as classifier neural networks.

In some embodiments, the facility displays some or all of its findings in connection with the image, such as in a pop-up window displaced over or beside the image. In some cases these include one or more of the quantitative attributes, and one or more qualitative attributes.

By operating in some or all of the ways described above, the facility obviates a great deal of decision making and manual work by an expert user required by conventional techniques for interpreting ultrasound images, permitting this activity to be quickly and successfully completed by less expert users.

Additionally, the facility improves the functioning of computer or other hardware, such as by reducing the dynamic display area, processing, storage, and/or data transmission resources needed to perform a certain task, thereby enabling the task to be permitted by less capable, capacious, and/or expensive hardware devices, and/or be performed with lesser latency, and/or preserving more of the conserved resources for use in performing other tasks. For example, by making the best use of an initial ultrasound image, the facility avoids many cases in which re-imaging is required. By reducing the need to reimage, the facility consumes, overall, less memory and processing resources to capture additional images. Also, by reducing the amount of time needed to successfully complete a single diagnostic session, the facility permits an organization performing ultrasound imaging to purchase fewer copies of an ultrasound apparatus to serve the same number of patients, or operate an unreduced number of copies at a lower utilization rate, which can extend their useful lifespan, improves their operational status at every time in their lifespan, reduces the need for intra-lifespan servicing and calibration, etc.

Further, for at least some of the domains and scenarios discussed herein, the processes described herein as being performed automatically by a computing system cannot practically be performed in the human mind, for reasons that include that the starting data, intermediate state(s), and ending data are too voluminous and/or poorly organized for human access and processing, and/or are a form not perceivable and/or expressible by the human mind; the involved data manipulation operations and/or subprocesses are too complex, and/or too different from typical human mental operations; required response times are too short to be satisfied by human performance; etc. For example, the computations performed by the facility to apply machine learning models are far too involved and extensive to practically be performed in the human mind.

FIG. 1 is a schematic illustration of a physiological sensing device 10, in accordance with one or more embodiments of the present disclosure. The device 10 includes a probe 12 that, in the illustrated embodiment, is electrically coupled to a handheld computing device 14 by a cable 17. The cable 17 includes a connector 18 that detachably connects the probe 12 to the computing device 14. The handheld computing device 14 may be any portable computing device having a display, such as a tablet computer, a smartphone, or the like. In some embodiments, the probe 12 need not be electrically coupled to the handheld computing device 14, but may operate independently of the handheld computing device 14, and the probe 12 may communicate with the handheld computing device 14 via a wireless communication channel.

The probe 12 is configured to transmit an ultrasound signal toward a target structure and to receive echo signals returning from the target structure in response to transmission of the ultrasound signal. The probe 12 includes an ultrasound sensor 20 that, in various embodiments, may include an array of transducer elements (e.g., a transducer array) capable of transmitting an ultrasound signal and receiving subsequent echo signals.

The device 10 further includes processing circuitry and driving circuitry. In part, the processing circuitry controls the transmission of the ultrasound signal from the ultrasound sensor 20. The driving circuitry is operatively coupled to the ultrasound sensor 20 for driving the transmission of the ultrasound signal, e.g., in response to a control signal received from the processing circuitry. The driving circuitry and processor circuitry may be included in one or both of the probe 12 and the handheld computing device 14. The device 10 also includes a power supply that provides power to the driving circuitry for transmission of the ultrasound signal, for example, in a pulsed wave or a continuous wave mode of operation.

The ultrasound sensor 20 of the probe 12 may include one or more transmit transducer elements that transmit the ultrasound signal and one or more receive transducer elements that receive echo signals returning from a target structure in response to transmission of the ultrasound signal. In some embodiments, some or all of the transducer elements of the ultrasound sensor 20 may act as transmit transducer elements during a first period of time and as receive transducer elements during a second period of time that is different than the first period of time (i.e., the same transducer elements may be usable to transmit the ultrasound signal and to receive echo signals at different times).

The computing device 14 shown in FIG. 1 includes a display screen 22 and a user interface 24. The display screen 22 may be a display incorporating any type of display technology including, but not limited to, LCD or LED display technology. The display screen 22 is used to display one or more images generated from echo data obtained from the echo signals received in response to transmission of an ultrasound signal, and in some embodiments, the display screen 22 may be used to display color flow image information, for example, as may be provided in a Color Doppler imaging (CDI) mode. Moreover, in some embodiments, the display screen 22 may be used to display audio waveforms, such as waveforms representative of an acquired or conditioned auscultation signal.

In some embodiments, the display screen 22 may be a touch screen capable of receiving input from a user that touches the screen. In such embodiments, the user interface 24 may include a portion or the entire display screen 22, which is capable of receiving user input via touch. In some embodiments, the user interface 24 may include one or more buttons, knobs, switches, and the like, capable of receiving input from a user of the ultrasound device 10. In some embodiments, the user interface 24 may include a microphone 30 capable of receiving audible input, such as voice commands.

The computing device 14 may further include one or more audio speakers 28 that may be used to output acquired or conditioned auscultation signals, or audible representations of echo signals, blood flow during Doppler ultrasound imaging, or other features derived from operation of the device 10.

The probe 12 includes a housing, which forms an external portion of the probe 12. The housing includes a sensor portion located near a distal end of the housing, and a handle portion located between a proximal end and the distal end of the housing. The handle portion is proximally located with respect to the sensor portion.

The handle portion is a portion of the housing that is gripped by a user to hold, control, and manipulate the probe 12 during use. The handle portion may include gripping features, such as one or more detents, and in some embodiments, the handle portion may have a same general shape as portions of the housing that are distal to, or proximal to, the handle portion.

The housing surrounds internal electronic components and/or circuitry of the probe 12, including, for example, electronics such as driving circuitry, processing circuitry, oscillators, beamforming circuitry, filtering circuitry, and the like. The housing may be formed to surround or at least partially surround externally located portions of the probe 12, such as a sensing surface. The housing may be a sealed housing, such that moisture, liquid or other fluids are prevented from entering the housing. The housing may be formed of any suitable materials, and in some embodiments, the housing is formed of a plastic material. The housing may be formed of a single piece (e.g., a single material that is molded surrounding the internal components) or may be formed of two or more pieces (e.g., upper and lower halves) which are bonded or otherwise attached to one another.

In some embodiments, the probe 12 includes a motion sensor. The motion sensor is operable to sense a motion of the probe 12. The motion sensor is included in or on the probe 12 and may include, for example, one or more accelerometers, magnetometers, or gyroscopes for sensing motion of the probe 12. For example, the motion sensor may be or include any of a piezoelectric, piezoresistive, or capacitive accelerometer capable of sensing motion of the probe 12. In some embodiments, the motion sensor is a tri-axial motion sensor capable of sensing motion about any of three axes. In some embodiments, more than one motion sensor 16 is included in or on the probe 12. In some embodiments, the motion sensor includes at least one accelerometer and at least one gyroscope.

The motion sensor may be housed at least partially within the housing of the probe 12. In some embodiments, the motion sensor is positioned at or near the sensing surface of the probe 12. In some embodiments, the sensing surface is a surface which is operably brought into contact with a patient during an examination, such as for ultrasound imaging or auscultation sensing. The ultrasound sensor 20 and one or more auscultation sensors are positioned on, at, or near the sensing surface.

In some embodiments, the transducer array of the ultrasound sensor 20 is a one-dimensional (1D) array or a two-dimensional (2D) array of transducer elements. The transducer array may include piezoelectric ceramics, such as lead zirconate titanate (PZT), or may be based on microelectromechanical systems (MEMS). For example, in various embodiments, the ultrasound sensor 20 may include piezoelectric micromachined ultrasonic transducers (PMUT), which are microelectromechanical systems (MEMS)-based piezoelectric ultrasonic transducers, or the ultrasound sensor 20 may include capacitive micromachined ultrasound transducers (CMUT) in which the energy transduction is provided due to a change in capacitance.

The ultrasound sensor 20 may further include an ultrasound focusing lens, which may be positioned over the transducer array, and which may form a part of the sensing surface. The focusing lens may be any lens operable to focus a transmitted ultrasound beam from the transducer array toward a patient and/or to focus a reflected ultrasound beam from the patient to the transducer array. The ultrasound focusing lens may have a curved surface shape in some embodiments. The ultrasound focusing lens may have different shapes, depending on a desired application, e.g., a desired operating frequency, or the like. The ultrasound focusing lens may be formed of any suitable material, and in some embodiments, the ultrasound focusing lens is formed of a room-temperature-vulcanizing (RTV) rubber material.

In some embodiments, first and second membranes are positioned adjacent to opposite sides of the ultrasound sensor 20 and form a part of the sensing surface. The membranes may be formed of any suitable material, and in some embodiments, the membranes are formed of a room-temperature-vulcanizing (RTV) rubber material. In some embodiments, the membranes are formed of a same material as the ultrasound focusing lens.

Figure 2:
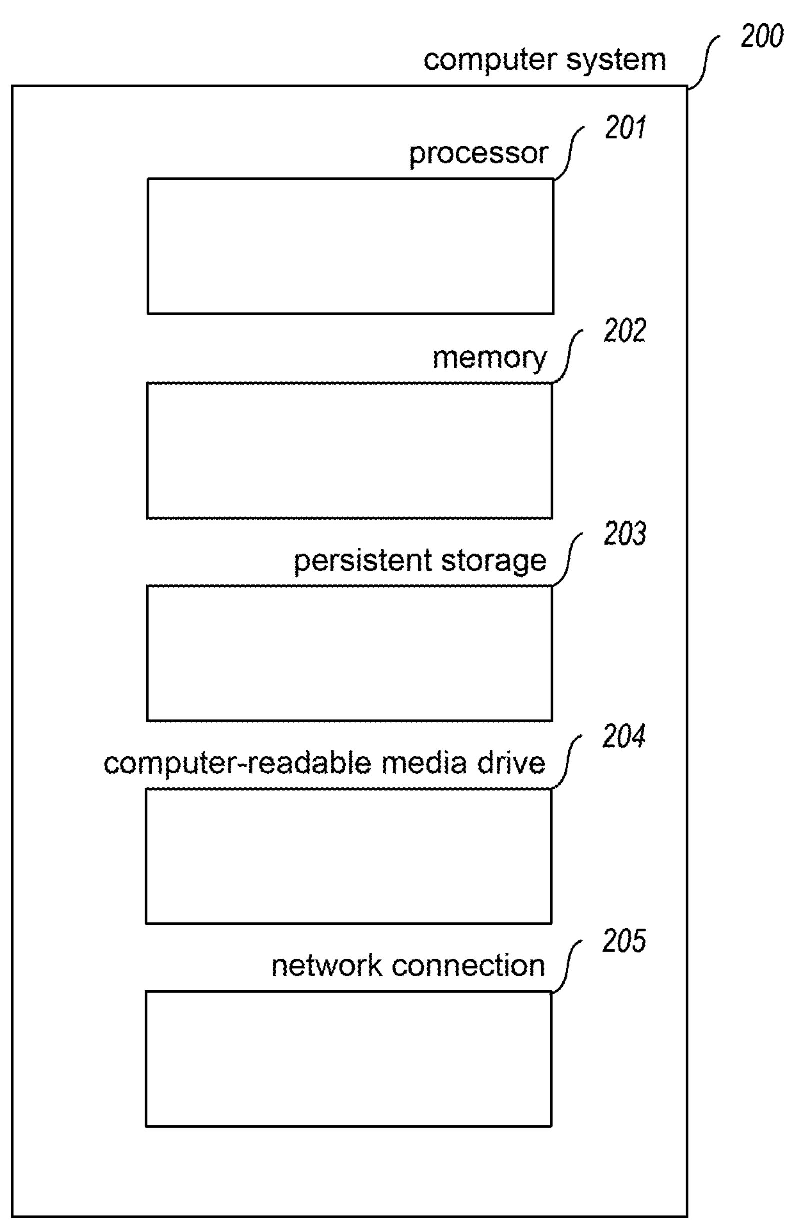
FIG. 2 is a block diagram showing some of the components typically incorporated in at least some of the computer systems and other devices on which the facility operates.

FIG. 2 is a block diagram showing some of the components typically incorporated in at least some of the computer systems and other devices on which the facility operates. In various embodiments, these computer systems and other devices 200 can include server computer systems, cloud computing platforms or virtual machines in other configurations, desktop computer systems, laptop computer systems, netbooks, mobile phones, personal digital assistants, televisions, cameras, automobile computers, electronic media players, physiological sensing devices, and/or their associated display devices, etc. In various embodiments, the computer systems and devices include zero or more of each of the following: a processor 201 for executing computer programs and/or training or applying machine learning models, such as a CPU, GPU, TPU, NNP, FPGA, or ASIC; a computer memory 202 for storing programs and data while they are being used, including the facility and associated data, an operating system including a kernel, and device drivers; a persistent storage device 203, such as a hard drive or flash drive for persistently storing programs and data; a computer-readable media drive 204, such as a floppy, CD-ROM, or DVD drive, for reading programs and data stored on a computer-readable medium; and a network connection 205 for connecting the computer system to other computer systems to send and/or receive data, such as via the Internet or another network and its networking hardware, such as switches, routers, repeaters, electrical cables and optical fibers, light emitters and receivers, radio transmitters and receivers, and the like. None of the components shown in FIG. 2 and discussed above constitute a data signal per se. While computer systems configured as described above are typically used to support the operation of the facility, those skilled in the art will appreciate that the facility may be implemented using devices of various types and configurations, and having various components.

Figure 3:
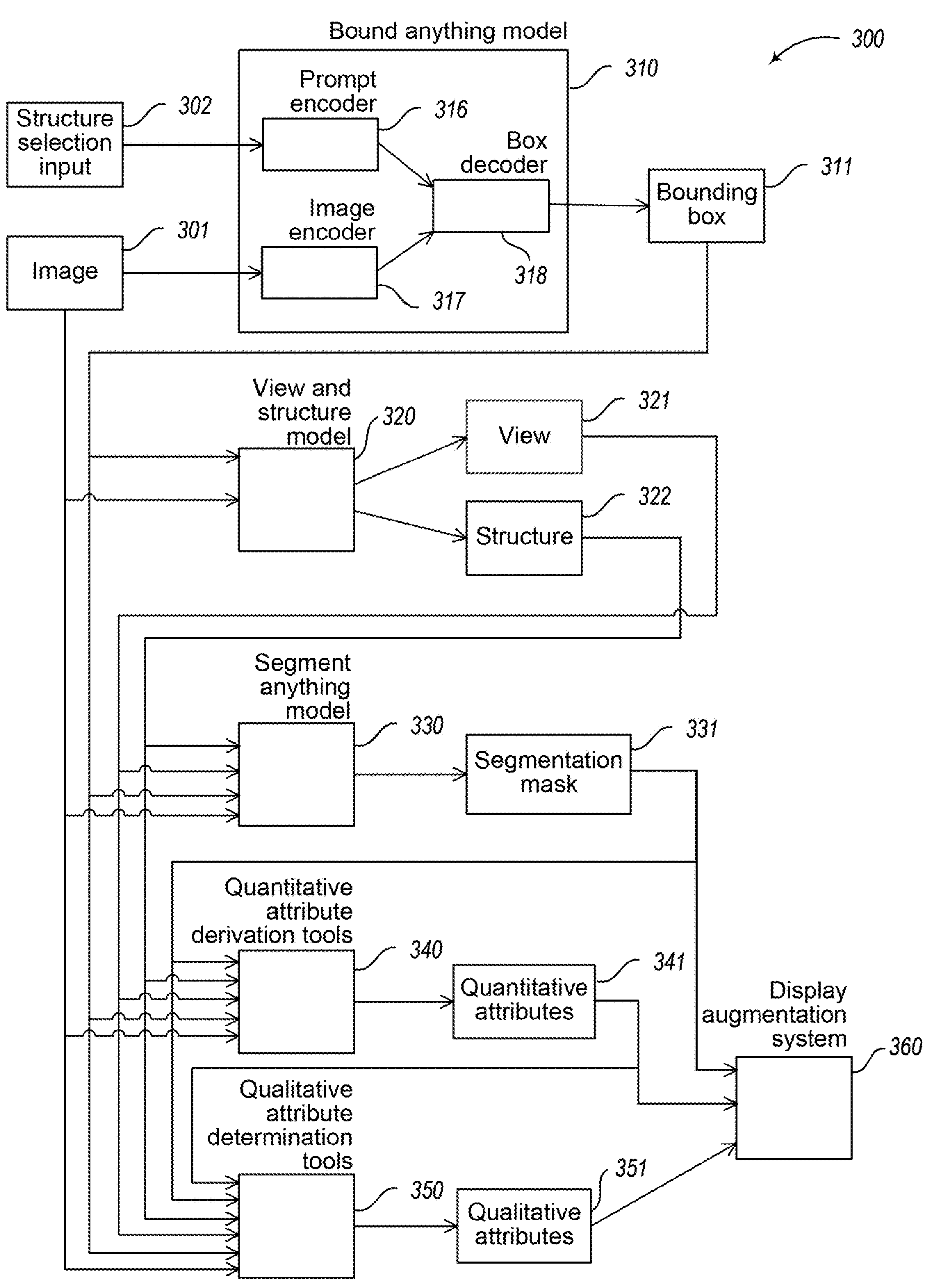
FIG. 3 is a data flow diagram showing the facility's processing of an ultrasound image and structure selection input originated by a user.

FIG. 3 is a data flow diagram showing the facility's processing of an ultrasound image and structure selection input originated by a user. An image 301 is received from an ultrasound device and displayed to a user. The user generates structure selection input 302 by interacting with the displayed image in a way that selects a structure visualized in the image, such as the left ventricle of the patient's heart. In various embodiments, this input takes various forms, such as by using a touchscreen, stylus, mouse, joystick, etc., to touch inside the anatomical structure, scribble over at least part of its area, draw a box or oval or other shape around it; panning or zooming the image to show the structure in the center of the image, etc.; speaking the name of the structure, or a location in the image where the structure occurs; etc.

The facility subjects the image and structure selection input to a bound anything model 310 to predict a bounding box 311 surrounding the selected structure. In some embodiments, the bound anything model is a deep learning model such as a convolutional neural network or transformer. In some embodiments, the bound anything model 310 includes a prompt encoder 316 that receives the structure selection input, and encodes it into a prompt embedding for use by a box decoder 318 of the bound anything model. In some embodiments, the prompt encoder is a neural network composed of embedding layers for point inputs, and a small convolutional downscaling neural network for scribbles. In various embodiments, the facility uses a variety of other architectures in the prompt encoder for input in a variety of other modes.

In some embodiments, the bound anything model further includes an image encoder 317 that transforms the image into an image embedding for use by the box decoder. In some embodiments, the image encoder is a vision transformer neural network optimized for real time inference on mobile devices, such as TinyViT (described by Kan Wu, Jinnian Zhang, Houwen Peng, Mengchen Liu, Bin Xiao, Jianlong Fu, Lu Yuan: "TinyViT: Fast Pretraining Distillation for Small Vision Transformers", 2022; [arxiv.org/abs/2207.10666 arXiv: 2207.10666]) or MobileViT (described by Sachin Mehta, Mohammad Rastegari: "MobileViT: Light-weight, General-purpose, and Mobile-friendly Vision Transformer", 2021; [arxiv.org/abs/2110.02178 arXiv: 2110.02178]), or it may be a convolutional neural network such as RepViT (described by Ao Wang, Hui Chen, Zijia Lin, Jungong Han, Guiguang Ding: "RepViT: Revisiting Mobile CNN From ViT Perspective", 2023; [arxiv.org/abs/2307.09283 arXiv: 2307.09283]) or MobileNetV3 (described by Andrew Howard, Mark Sandler, Grace Chu, Liang-Chieh Chen, Bo Chen, Mingxing Tan, Weijun Wang, Yukun Zhu, Ruoming Pang, Vijay Vasudevan, Quoc V. Le, Hartwig Adam: "Searching for MobileNetV3", 2019; [arxiv.org/abs/1905.02244]).

The box decoder receives the encoded structure selection input from the prompt encoder and the image embedding from the image encoder, and predicts a bounding box for the selected structure. In some embodiments, the box decoder is composed of a two-way transformer for merging the outputs of the image encoder and prompt encoder, followed by a transformer decoder with feedword prediction heads to generate bounding boxes as in DETR (described by Nicolas Carion, Francisco Massa, Gabriel Synnaeve, Nicolas Usunier, Alexander Kirillov, Sergey Zagoruyko: "End-to-End Object Detection with Transformers", 2020; [arxiv.org/abs/2005.12872 arXiv: 2005.12872]), or followed by a transformer decoder with an upscaling convolutional neural network with prediction heads to generate bounding boxes as in YOLOv3 (described by Joseph Redmon, Ali Farhadi: "YOLOv3: An Incremental Improvement", 2018; [arxiv.org/abs/1804.02767 arXiv: 1804.02767]).

In some embodiments, the facility trains and applies different versions of the bound anything model that are fine-tuned to different anatomical areas of interest—such as the heart, liver, and kidney—using training data sets from those anatomical regions to improve precision and accuracy. In some embodiments, this fine tuning uses transfer learning, such that a model previously trained on a superset of images is adapted to a smaller specific set of images.

The facility subjects the image in the bounding box produced by the bound anything model to a view and structure model 320 to identify a view 321 from which the image was captured, and the structure 322 selected by the structure selection input that is within the bounding box. In some embodiments, the view and structure model uses a hierarchical classification approach, in which a first level of the model identifies the view, and a second level of the model identifies one or more specific objects within the view. In some embodiments, the model is a deep learning model such as a convolutional neural network or transformer that takes as input the full B-mode ultrasound image or a cropped region of that image corresponding to the predicted bounding box and returns classification results for view and structure. In some embodiments, the bound anything model 310 and view and structure model 320 are known collectively as a "Stage 1" model.

Figure 4:
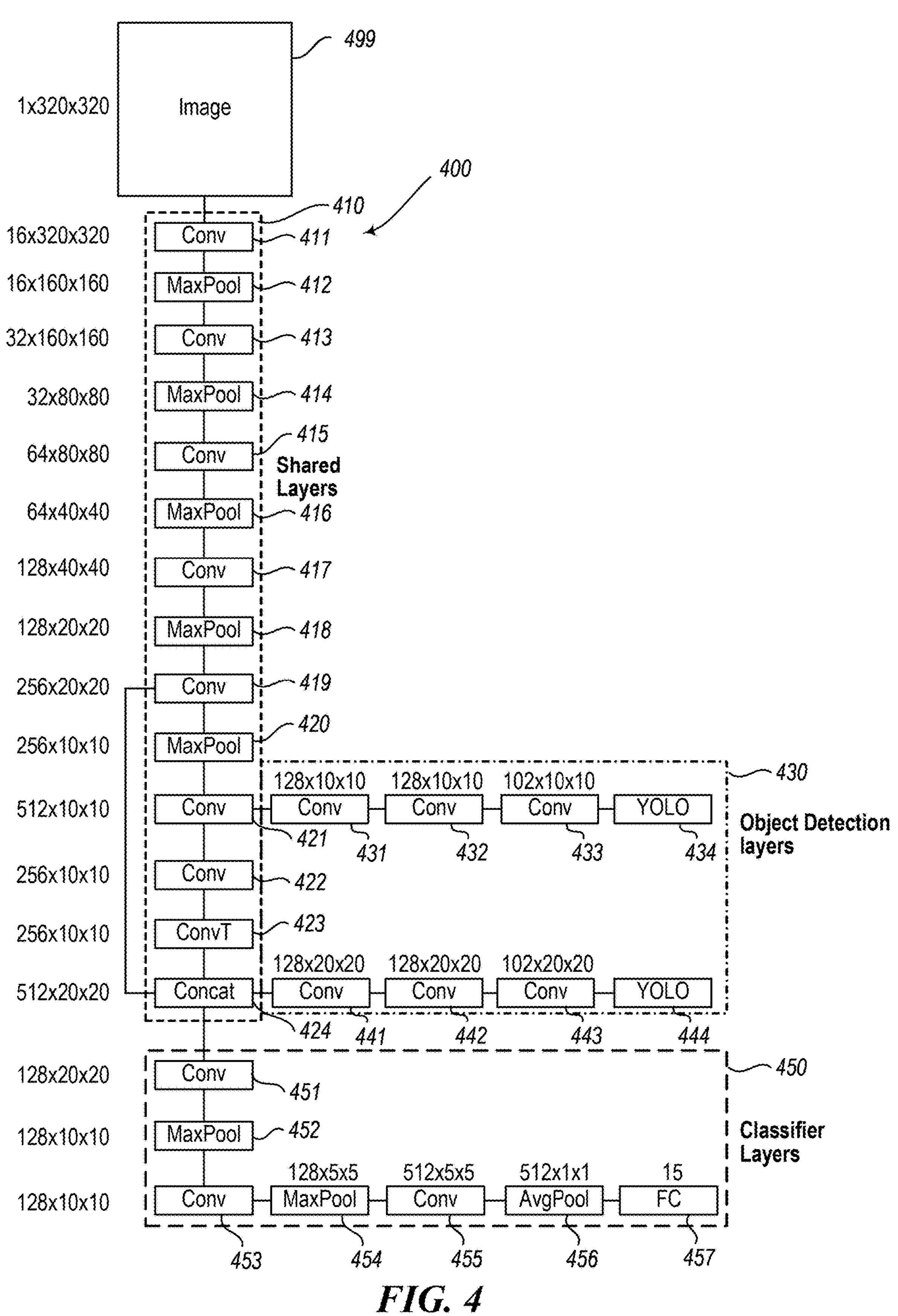
FIG. 4 is a model diagram showing a model architecture used by the facility in some embodiments for its view and structure model.

FIG. 4 is a model diagram showing a model architecture used by the facility in some embodiments for its view and structure model. The model architecture 400 includes shared layers 410 used by the facility both for structure detection and view classification; object detection layers 430 used by the facility only to perform structure detection; and classifier layers 450 used by the facility only to perform view classification. For each of the layers, FIG. 4 shows a layer type and layer size. Layer type is expressed in terms of the following abbreviations:

TABLE 1

| Abbreviation | Layer Type |
|---|---|
| AvgPool | Average Pooling layer |
| Concat | Concatenation layer |
| Conv | Convolutional layer |
| ConvT | Transposed Convolutional layer |
| FC | Fully-Connected layer |
| MaxPool | Maximum Pooling layer |
| YOLO | You Only Look Once layer |

For example, layer 411, shown with the type abbreviation "Conv," is a Convolutional layer. Layer size is expressed with the dimensions number of output values per pixel×number of pixels in horizontal dimension×number of pixels in vertical dimension. For example, layer 411, shown with the dimensions 16×320×320, outputs 16 values per pixel, in a rectangular array of 320 pixels by 320 pixels. Those skilled in the art will appreciate that the layers and their orders and dimensions may be varied in various ways.

Returning to FIG. 3, the facility subjects some or all of the following data to its segment anything model 330 to generate a segmentation mask 331 identifying the pixels of the image that make up the selected structure: The image, the structure selection input 302, the bounding box determined by the bound anything model, the view determined by the view and structure model, and the structure determined by the view and structure model. In some embodiments, the Segment Anything Model (SAM) is zero-shot foundational image segmentation model that segments arbitrary objects given a user prompt (described in Kirillov, A., Mintun, E., Ravi, N., Mao, H., Rolland, C., Gustafson, L., Xiao, T., Whitehead, S., Berg, A. C., Lo, W. Y. and Dollar, P., 2023. Segment anything. In Proceedings of the IEEE/CVF International Conference on Computer Vision (pp. 4015-4026)). An original SAM was designed to segment objects in natural images and was modified to be used in medical images in the MedSAM model (described in Mazurowski, M. A., Dong, H., Gu, H., Yang, J., Konz, N. and Zhang, Y., 2023. Segment anything model for medical image analysis: an experimental study. Medical Image Analysis, 89, p. 102918). MedSAM was designed to segment structures in medical images given a bounding box as a user prompt. In some embodiments, the segment anything model 330 is known as a "Stage 2" model.

Like the methodology used in MedSAM, Stage 2 uses a SAM-style model trained on medical domain datasets to produce a model that accurately segments structures within a bounding box. Rather than a user-provided bounding box, this stage uses the bounding box predicted in Stage 1. Additionally, the structure selection input 302, the ultrasound view 321, and structure names 322 may be used as additional inputs to the model to improve segmentation accuracy.

In some embodiments, to make it better able to run in real-time on limited computing hardware, the SAM architecture is modified in ways to decrease inference time for the model. In various embodiments, these modifications include one or more of reducing number of model parameters, decreasing model depth (number of layers) and width (number of channels), and replacement of transformer modules with more efficient convolutional layers. To incorporate temporal information, the architecture may also incorporate image embeddings from neighboring frames, like the methodology used in SAM 2: Segment Anything in Images and Videos (described in Ravi, N., Gabeur, V., Hu, Y.-T., Hu, R., Ryali, C., Ma, T., Khedr, H., Radle, R., Rolland, C., Gustafson, L., Mintun, E., Pan, J., Alwala, Kalyan Vasudev, Carion, N., Wu, C.-Y., Girshick, R., Dollár, P., & Feichtenhofer, C. (2024). *SAM 2: Segment Anything in Images and Videos*. ArXiv.org. arxiv.org/abs/2408.00714).

In some embodiments (not shown) the facility collapses the bound anything model, view and structure model, and segment anything model into a single model that transforms the image and structure selection input into a segmentation mask, or into a structure identity and a segmentation mask.

The facility subjects some or all of the following data to quantitative attribute derivation tools 340 in order to derive quantitative attributes 341 of the selected structure based upon its appearance in the image: the image, the bounding box, the view, the structure, and the segmentation task.

In some embodiments, these quantitative attributes derivation tools count a linear series of pixels corresponding to a distance, or a two-dimensional grouping of pixels corresponding to a cross-sectional area. In some cases, the tools use a similar approach to count pixels in three dimensions corresponding to a volume that are distributed across a series of images each corresponding to a different anatomical plane.

The segmentation mask from Stage 2 traces the border of the anatomy of interest selected in Stage 1. In Stage 3, the segmentation mask is analyzed to automatically extract quantitative attributes such as dimensions, volumes, and other clinically relevant measurements to the anatomy of interest. For example, in cardiac imaging this could involve calculating the end-diastolic volume (EDV), end-systolic volume (ESV), ejection fraction (EF), wall thickness, strain measurements, and wall motion abnormalities. The specific set of measurements and calculations to be performed is determined by the identified view and structure name.

Geometric and morphological analysis techniques may be applied to ensure the measurements are accurate. For example, a contour-fitting algorithm may be used to refine the boundaries of the segmentation mask to produce more precise and accurate volume calculations. To ensure reliability of the derived measurements, error estimation processes may also be incorporated. This may involve comparing the derived measurements to known reference values or employing statistical models to predict expected range of values. If the derived measurements fall outside the expected range, an automatic correction process may be triggered. This process may involve re-segmenting the structure of interest or prompting the user to manually adjust the measurement.

The facility subjects some or all of the following data to qualitative attribute determination tools 350 in order to determine qualitative attributes 351 for the selected structure as shown in the image: the image, bounding box, view, structure, segmentation mask and quantitative attributes. The outputs of this stage are a classification of qualitative attributes related to the bounded structure, including potential diseases and pathologies, along with confidence scores and explanatory visualizations. In this stage, a classifier model classifies the segmented structure to identify potential diseases or pathologies. For example, it may detect hypertrophy, dilation, or reduced function in cardiac structures. The model itself may be a deep learning model such as a convolutional neural network or transformer trained on large datasets with annotated cases of various pathologies.

As one example, to assess the qualitative attribute of endocardial hypertrophy, the facility uses an endocardial thickness measurement among the quantitative attributes determined by the facility, and compares it to the appropriate entry in a lookup table of maximum healthy thicknesses that considers such relevant additional patient attributes as gender, phenotype, and body surface area.

To improve the robustness of disease and pathology classification, the model may incorporate multi-modal data such as patient history, lab results, or other imaging modalities. This may allow the model to make informed decisions considering a broader clinical context. In some embodiments, each classification result is accompanied by a confidence score that indicates the likelihood of the pathology. The confidence score is calculated based on the model's internal features and decision processes. To enhance the interpretability of the results, the model may generate attention maps that highlight the regions of the image that contributed most to the classification decision. These maps may be displayed alongside the disease and pathology predictions to help medical experts understand the rationale behind the model's predictions.

A display augmentation system 360 receives some or all of the following data in order to generate an augmented version of the image's display: the segmentation mask, the quantitative attributes, and the qualitative attributes. This stage takes as input the quantitative and qualitative results of Stage 3 and 4, and outputs a dialogue box displaying information that information with options for user interaction, customization, and further analysis.

A comprehensive dialogue box is presented to the user, displaying the extracted information, including measurements, identified diseases, and any relevant confidence scores. The interface is designed to be user-friendly and customizable, allowing clinicians to focus on the most critical information. The dialogue box may also provide links to related cases or literature, offering the clinician additional resources to support their decision-making process. Furthermore, it may include options for exporting the results to the patient's electronic medical record (EMR) system or for further analysis in specialized software.

In some embodiments, the interface enables users to interact with the results, such as adjusting the segmentation mask or re-running specific stages of the analysis with modified parameters. This flexibility ensures that the tool can accommodate the specific needs and preferences of different clinicians. Additionally, the interface may include a feature for real-time collaboration, enabling multiple clinicians to review and discuss the results simultaneously, regardless of their physical location.

Figure 5:
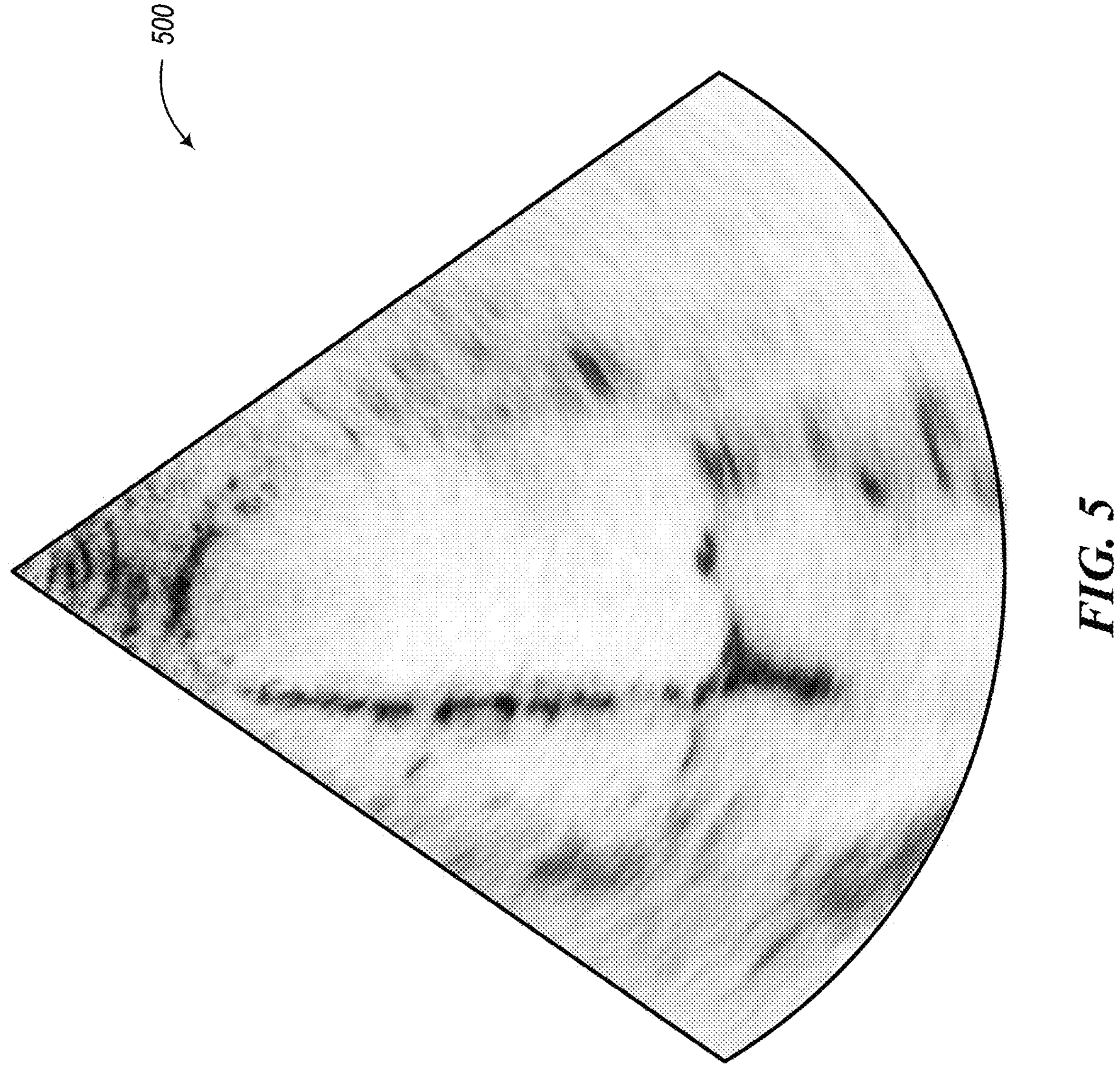
FIG. 5 is a medical imaging diagram showing a sample patient image accessed by the facility.

FIG. 5 is a medical imaging diagram showing a sample patient image accessed by the facility. The patient image 500 is an ultrasound image. This ultrasound image, also shown in FIGS. 6-9 discussed below, has been grayscale-inverted in order to be more easily and faithfully produced in patent drawings. The ultrasound image is a cardiac image visualizing the patient's left ventricle.

Figure 6:
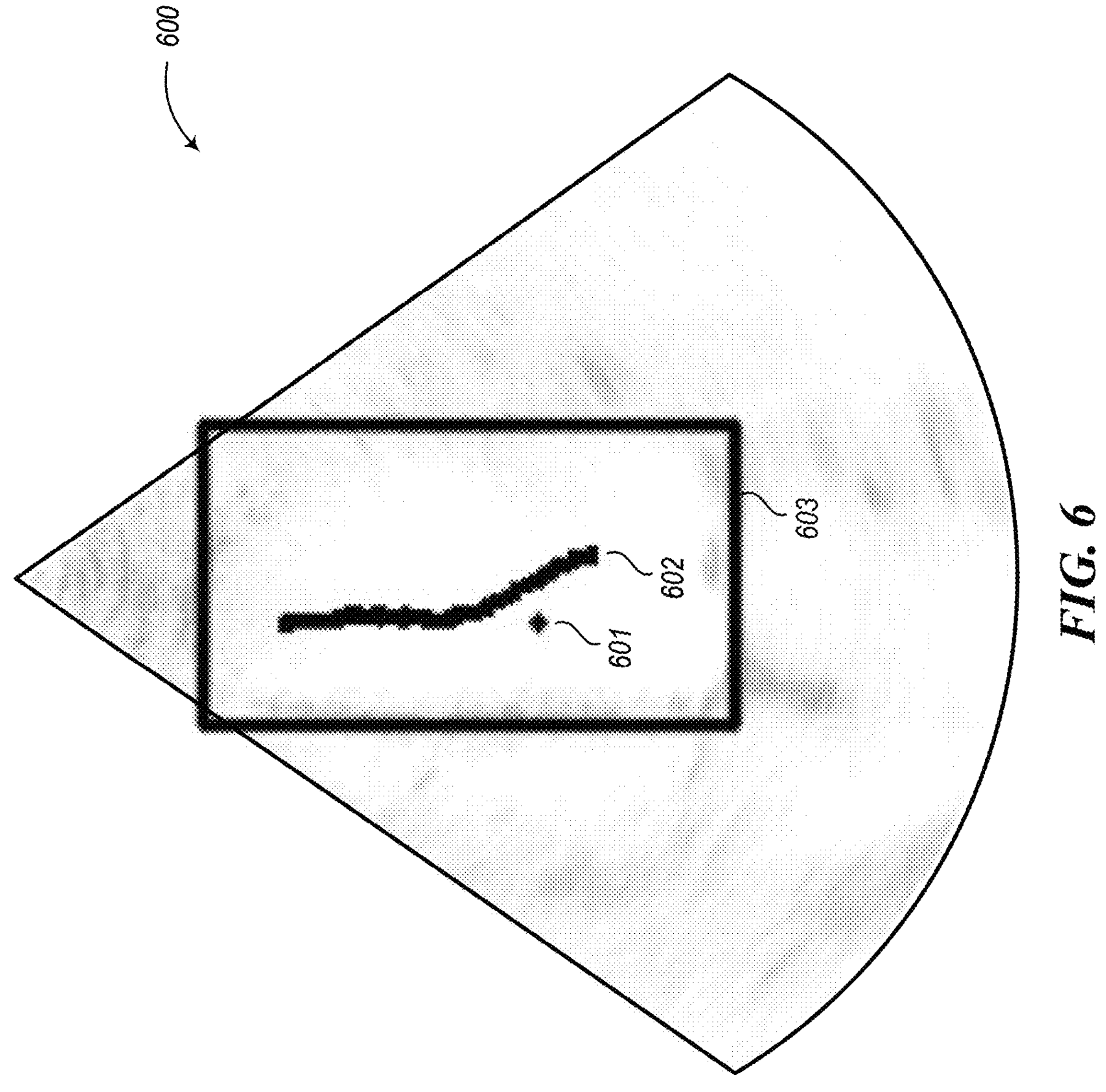
FIG. 6 is a medical imaging diagram showing a version of the sample patient image together with sample structure selection input from a user selecting a left ventricle structure visualized in the image.

FIG. 6 is a medical imaging diagram showing a version of the sample patient image together with sample structure selection input from a user selecting a left ventricle structure visualized in the image. Relative to the image 600, there can be seen three alternative forms of user input selecting the left ventricle structure: a single point 601 placed within the left ventricle structure; a scribble 602 occupying some of the area of the left ventricle structure; and a rectangle 603 drawn to contain the left ventricle structure.

Figure 7:
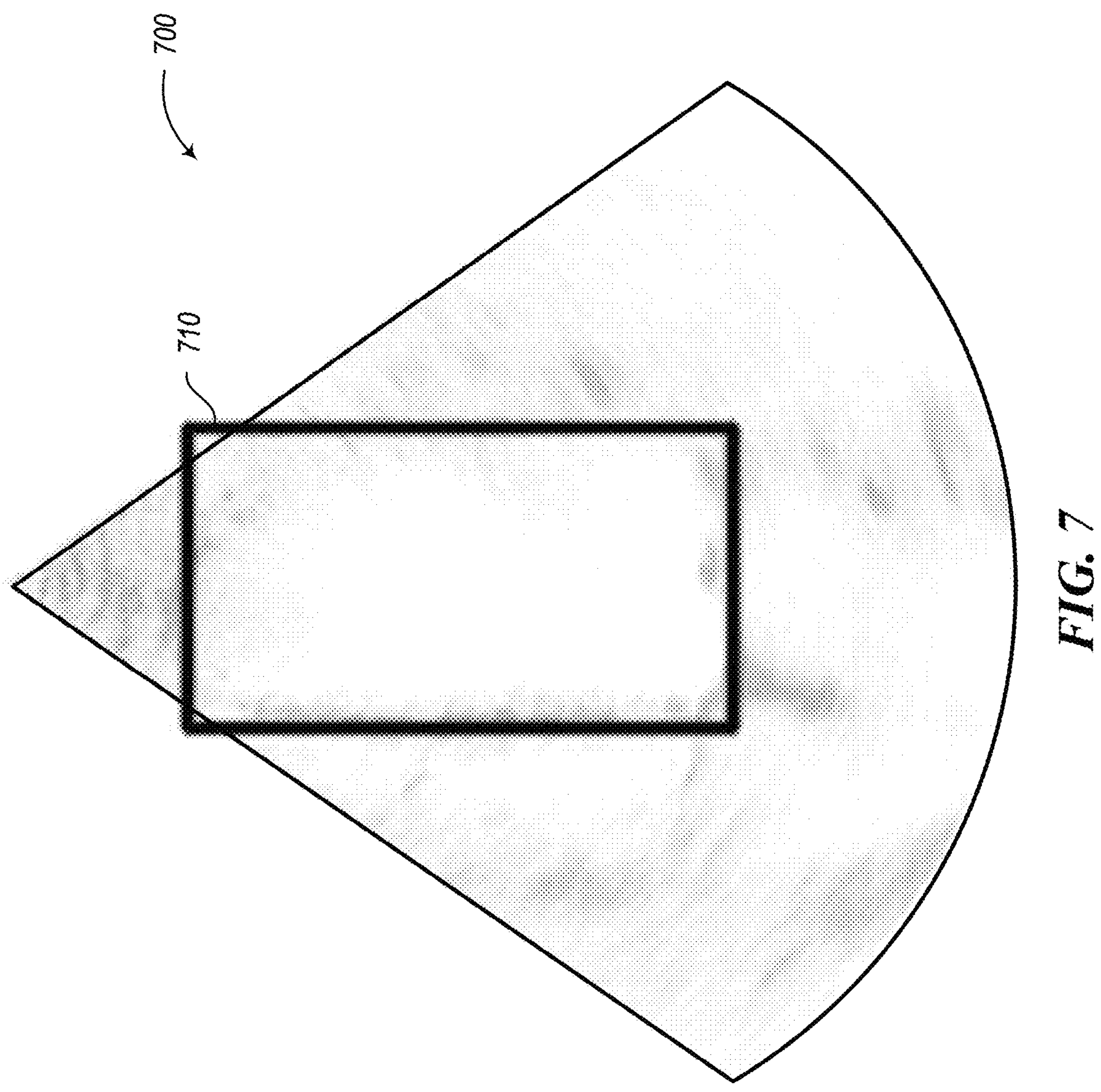
FIG. 7 is a medical imaging diagram showing a bounding box determined by the facility for the left ventricle structure selected by the sample input with respect to the sample image.

FIG. 7 is a medical imaging diagram showing a bounding box determined by the facility for the left ventricle structure selected by the sample input with respect to the sample image. The image 700 shows a bounding box rectangle 710 predicted by the facility based on any of the forms of structure selection input shown in FIG. 6.

Figure 8:
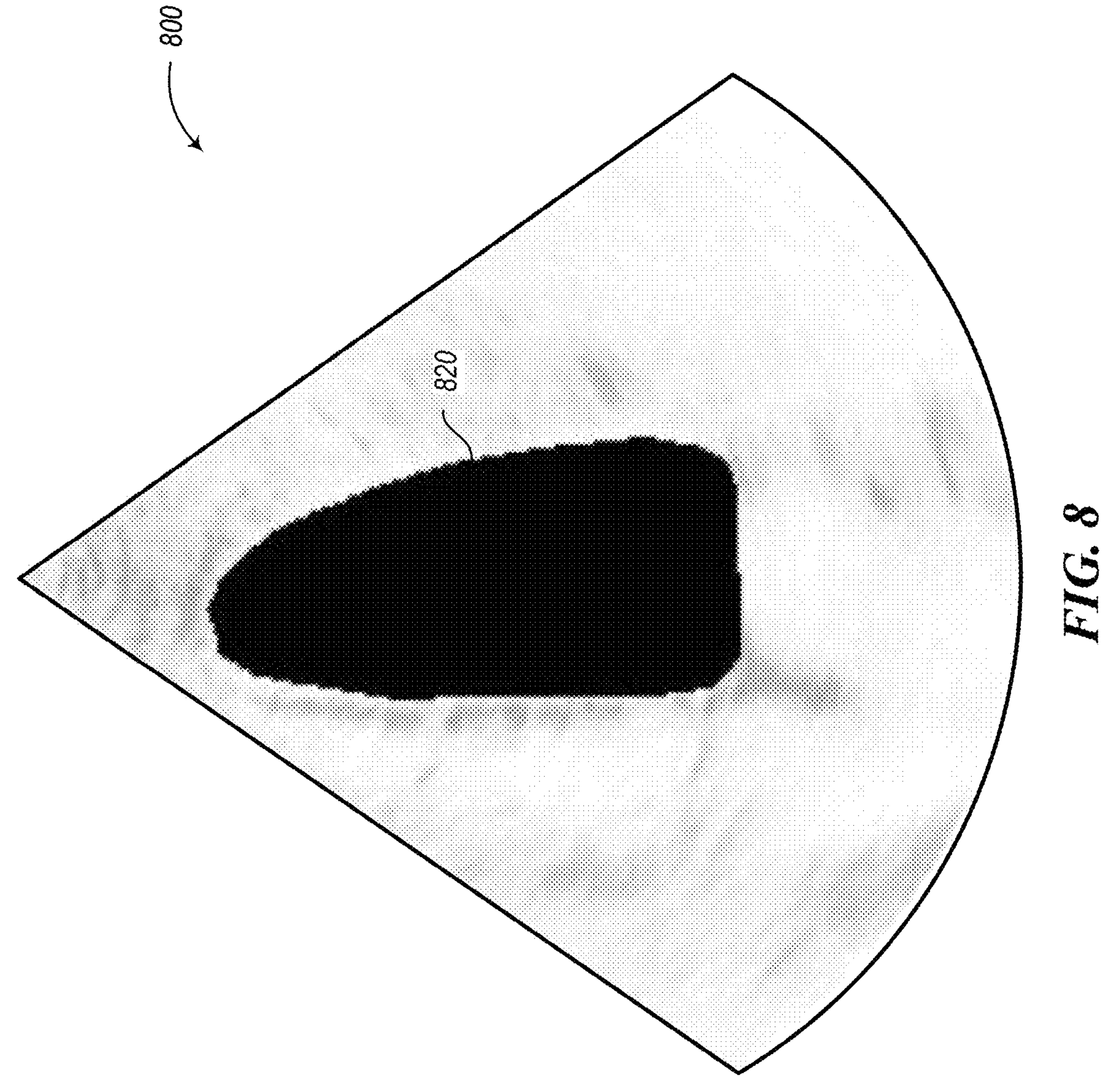
FIG. 8 is a medical imaging diagram showing the sample patient image overlaid by a segmentation mask determined by the facility for the sample image.

FIG. 8 is a medical imaging diagram showing the sample patient image overlaid by a segmentation mask determined by the facility for the sample image. The segmentation mask 820 shows in a dark shade the pixels predicted to visualize the selected left ventricle structure.

Figure 9:
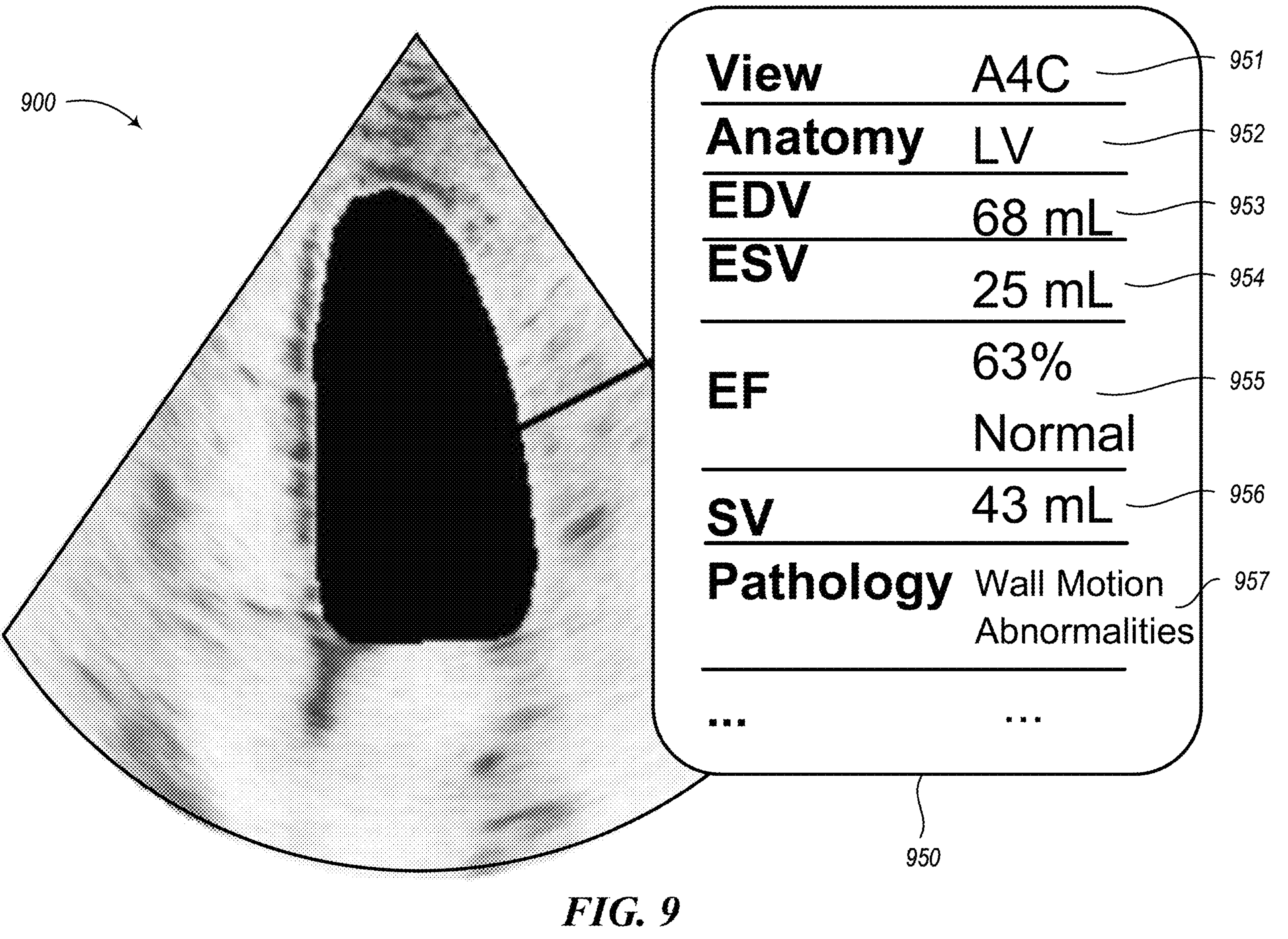
FIG. 9 is a medical imaging diagram showing a sample augmented display presented by the facility, in which the ultrasound image is displayed together with data automatically determined by the facility with respect to the image and its visualization of the selected structure.

FIG. 9 is a medical imaging diagram showing a sample augmented display presented by the facility, in which the ultrasound image is displayed together with data automatically determined by the facility with respect to the image and its visualization of the selected structure. While the selected structure is shown overlaid with an opaque version of the segmentation mask in FIG. 9, in some embodiments (not shown) the selected structure is shown in a way that makes visible its visual details in the original ultrasound image, such as by drawing a border around the exterior of the segmentation mask, tinting the pixels of the original ultrasound image intersecting with the segmentation mask in a particular tint or hue, etc. An information window 950 includes information such as the view 951 from which the facility predicts the image was captured: A4C, short for apical 4 chamber; a name 952 identifying the selected structure: LV, short for left ventricle; four quantitative attributes determined by the facility for the left ventricle based upon the image, an end-diastolic volume (EDV) 953, an end-systolic volume (ESV) 954, an ejection fraction (EF) 955, and a stroke volume (SV) 956. The window also includes a qualitative attribute determined by the facility, an indicated pathology 957 of wall motion abnormalities.

While the display diagrams discussed above show a display whose formatting, organization, informational density, etc., is best suited to certain types of display devices, those skilled in the art will appreciate that actual displays presented by the facility may differ from those shown, in that they may be optimized for particular other display devices, or have shown visual elements omitted, visual elements not shown included, visual elements reorganized, reformatted, revisualized, or shown at different levels of magnification, etc.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system, comprising:

an ultrasound sensing device; and a computing device, the computing device comprising:

- a communication interface configured to directly receive ultrasound echo data sensed by the ultrasound sensing device from a patient, the received ultrasound echo data comprising an ultrasound image;
- a memory configured to:
  - store one or more neural networks each trained to analyze ultrasound images;
- a processor configured to:
  - cause the ultrasound image to be displayed;
  - receive input originating from a user specifying one or more points within the displayed ultrasound image;
  - subject to a first neural network inputs comprising the ultrasound image and the received input to obtain a bounding box within the ultrasound image inferred to surround an anatomical feature of interest;
  - subject to a second neural network inputs comprising the ultrasound image and the obtained bounding box to obtain an identity of the anatomical feature of interest;
  - subject to a third neural network inputs comprising the ultrasound image, the obtained bounding box, and the obtained feature identity to obtain a segmentation mask identifying pixels of the ultrasound image visualizing the anatomical feature of interest;
  - subject to one or more first tools inputs comprising the ultrasound image, the obtained bounding box, the obtained feature identity, and the segmentation mask to obtain one or more quantitative attributes of the anatomical feature of interest;
  - subject to one or more second tools inputs comprising the ultrasound image, the obtained bounding box, the obtained feature identity, and the segmentation mask to obtain one or more qualitative attributes of the anatomical feature of interest; and
  - cause to be displayed simultaneously with the ultrasound image the obtained one or more quantitative attributes of the anatomical feature of interest and the obtained one or more qualitative attributes of the anatomical feature of interest.

2. The system of claim 1, the processor further configured to cause to be displayed simultaneously with (1) the ultrasound image, (2) the obtained one or more quantitative attributes of the anatomical feature of interest, and (3) the obtained one or more qualitative attributes of the anatomical feature of interest visual information identifying the pixels of the ultrasound image identified by the segmentation mask.

3. The system of claim 1 wherein the received input specifies at least one point within the anatomical feature of interest.

4. The system of claim 1 wherein the received input specifies a plurality of points representing one or more scribbles within the anatomical feature of interest.

5. The system of claim 1 wherein the received input specifies a plurality of points comprising a shape enclosing the anatomical feature of interest.

6. The system of claim 1 wherein the received input is speech naming the anatomical feature of interest.

7. The system of claim 1 wherein the feature of interest is an organ, a structure within an organ, a void within an organ, or a region of an organ.

8. The system of claim 1 wherein the obtained one or more quantitative attributes of the anatomical feature of interest comprise one or more of:

one or more dimensions,
one or more volumes,
one or more cross-sectional areas,
one or more volumetric flow rates,
end-diastolic volume,
end-systolic volume,
stroke volume,
ejection fraction,
wall thickness, and/or
strain measurement.

9. The system of claim 1 wherein the obtained one or more qualitative attributes of the anatomical feature of interest comprise one or more of:

disease indication;
pathology indication;
hypertrophy,
dilation, and/or
reduced cardiac function.

10. The system of claim 1 wherein subjecting to a first neural network inputs comprising the ultrasound image and the received input to obtain a bounding box within the ultrasound image inferred to surround an anatomical feature of interest comprises:

subjecting the ultrasound image to a fourth neural network to obtain an embedding of the ultrasound image;

subjecting the received input to a fifth neural network to obtain an encoding of the received input; and subjecting to a sixth neural network inputs comprising the obtained embedding and encoding to obtain the bounding box.

11. A method in a computing system, comprising:

receiving an ultrasound image;

causing the ultrasound image to be displayed;

receiving input originating from a user specifying one or more points within the displayed ultrasound image;

subjecting to a first neural network inputs comprising the ultrasound image and the received input to obtain, with respect to an anatomical feature of interest selected by the received input, an identity of the anatomical feature of interest and a segmentation mask identifying pixels of the ultrasound image visualizing the anatomical feature of interest;

subjecting to one or more first tools inputs comprising the ultrasound image, and the obtained feature identity to obtain one or more quantitative attributes of the anatomical feature of interest; and subjecting to one or more second tools inputs comprising the ultrasound image and the obtained feature identity, and the segmentation mask to obtain one or more qualitative attributes of the anatomical feature of interest.

12. The method of claim 11, further comprising:

causing to be displayed simultaneously with the ultrasound image the obtained one or more quantitative attributes of the anatomical feature of interest and the obtained one or more qualitative attributes of the anatomical feature of interest.

13. The method of claim 12, further comprising:

causing to be displayed simultaneously with (1) the ultrasound image, (2) the obtained one or more quantitative attributes of the anatomical feature of interest, and (3) the obtained one or more qualitative attributes of the anatomical feature of interest visual information identifying the pixels of the ultrasound image identified by the segmentation mask.

14. The method of claim 11 wherein subjecting the first neural network to inputs comprises:

subjecting to a second neural network inputs comprising the ultrasound image and the received input to obtain a bounding box within the ultrasound image inferred to surround the anatomical feature of interest;

subjecting to a third neural network inputs comprising the ultrasound image and the obtained bounding box to obtain the identity of the anatomical feature of interest; and subjecting to a fourth neural network inputs comprising the ultrasound image, the obtained bounding box, and the obtained feature identity to obtain the segmentation mask.

15. One or more hardware memories collectively having contents configured to cause a computer system to perform a method, the method comprising:

accessing an ultrasound image;

causing the ultrasound image to be displayed;

receiving input originating from a user specifying one or more points within the displayed ultrasound image;

subjecting to a first neural network inputs comprising the ultrasound image and the received input to obtain, with respect to an anatomical feature of interest selected by the received input, an identity of the anatomical feature of interest and a segmentation mask identifying pixels of the ultrasound image visualizing the anatomical feature of interest;

subjecting to one or more first tools inputs comprising the ultrasound image, and the obtained feature identity to obtain one or more quantitative attributes of the anatomical feature of interest; and subjecting to one or more second tools inputs comprising the ultrasound image and the obtained feature identity to obtain one or more qualitative attributes of the anatomical feature of interest.

16. The one or more memories of claim 15, the method further comprising:

causing to be displayed simultaneously with the ultrasound image the obtained one or more quantitative attributes of the anatomical feature of interest and the obtained one or more qualitative attributes of the anatomical feature of interest.

17. The one or more memories of claim 16, the method further comprising:

causing to be displayed simultaneously with (1) the ultrasound image, (2) the obtained one or more quantitative attributes of the anatomical feature of interest, and (3) the obtained one or more qualitative attributes of the anatomical feature of interest visual information identifying the pixels of the ultrasound image identified by the segmentation mask.

18. The one or more memories of claim 15 wherein subjecting the first neural network to inputs comprises:

subjecting to a second neural network inputs comprising the ultrasound image and the received input to obtain a bounding box within the ultrasound image inferred to surround the anatomical feature of interest;

subjecting to a third neural network inputs comprising the ultrasound image and the obtained bounding box to obtain the identity of the anatomical feature of interest; and subjecting to a fourth neural network inputs comprising the ultrasound image, the obtained bounding box, and the obtained feature identity to obtain the segmentation mask.

19. A system, comprising:

an ultrasound sensing device; and a computing device, the computing device comprising:

a communication interface configured to directly receive ultrasound echo data sensed by the ultrasound sensing device from a patient, the received ultrasound echo data comprising an ultrasound image;

a memory configured to:

store one or more neural networks each trained to analyze ultrasound images;

a processor configured to:

cause the ultrasound image to be displayed;

receive input originating from a user specifying one or more points within the displayed ultrasound image;

subject to a first neural network inputs comprising the ultrasound image and the received input to obtain, with respect to an anatomical feature of interest selected by the received input, an identity of the anatomical feature of interest and a segmentation mask identifying pixels of the ultrasound image visualizing the anatomical feature of interest;

subject to one or more first tools inputs comprising the ultrasound image and the obtained feature identity to obtain one or more quantitative attributes of the anatomical feature of interest; and subject to one or more second tools inputs comprising the ultrasound image and the obtained feature identity to obtain one or more qualitative attributes of the anatomical feature of interest.

20. The system of claim 19, the processor further configured to:

causing to be displayed simultaneously with the ultrasound image the obtained one or more quantitative attributes of the anatomical feature of interest and the obtained one or more qualitative attributes of the anatomical feature of interest.

* * * * *